(12) United States Patent
Deutschman et al.

(10) Patent No.: US 9,155,741 B2
(45) Date of Patent: Oct. 13, 2015

(54) METHODS OF USING A METHYLXANTHINE COMPOUND

(75) Inventors: Clifford S. Deutschman, Narbert, PA (US); Richard J. Levy, New York, NY (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1022 days.

(21) Appl. No.: 13/000,184

(22) PCT Filed: Jun. 29, 2009

(86) PCT No.: PCT/US2009/049086
§ 371 (c)(1),
(2), (4) Date: Sep. 14, 2011

(87) PCT Pub. No.: WO2009/158713
PCT Pub. Date: Dec. 30, 2009

(65) Prior Publication Data
US 2012/0004248 A1    Jan. 5, 2012

Related U.S. Application Data

(60) Provisional application No. 61/129,454, filed on Jun. 27, 2008.

(51) Int. Cl.
*A61K 31/4985* (2006.01)
*A61K 31/522* (2006.01)

(52) U.S. Cl.
CPC .................................. *A61K 31/522* (2013.01)

(58) Field of Classification Search
CPC .................................................. A61K 31/4985
USPC ..................................................... 514/262.1
See application file for complete search history.

(56) References Cited

U.S. PATENT DOCUMENTS

| 4,364,922 A | 12/1982 | Berne et al. |
| 2003/0012776 A1 | 1/2003 | Chin |

FOREIGN PATENT DOCUMENTS

| WO | WO 02/09583 A2 | 2/2002 |
| WO | WO 02/069977 A1 | 9/2002 |

OTHER PUBLICATIONS

Jones, molecular pharmacology, vol. 74, No. 3, pp. 673-684, online before print Jun. 26, 2008.*
Wang et al., "Pentoxifylline protects against endotoxin-induced acute renal failure in mice", Am J Physiol Renal Physiol 291: F1090-F1095, 2006.
Oliveira-Junior et al., "Effect of pentoxifylline on lung inflammation and gas exchange in a sepsis-induced acute lung injury model" Brazilian Journal of Medical and Biological Research, 2006, 39: 1455-1463.
Lira et al., "Cyclic adenosine monophosphate-phosphodiesterase inhibitors reduce skeletal muscle protein catabolism in septic rats", SHOCK vol. 27, No. 6, pp. 687-694, 2007.
Horrigan et al., "Immunomodulatory effects of caffeine: Friend or foe?", Pharmacology & Therapeutics 111 (2006) 877-892.
Coimbra et al., "Nonspecific phosphodiesterase inhibition attenuates liver injury in acute endotoxemia", Surgical Infections, vol. 6, No. 1, 2005, pp. 73-85.
Sefton, 1987, "Implantable pumps." CRC Crit. Ref. Biomed. Eng. 14:201.
Buchwald et al. "Long-term, continuous intravenous heparin administration by an implantable infusion pump in ambulatory patients with recurrent venous thrombosis."Surgery 88:507 (1980).
Saudek et al."A preliminary trial of the programmable implantable medication system for insulin delivery." N. Engl. J. Med. 321:574 (1989).
Goodson, in Medical Applications of controlled Release, supra, vol. 2, pp. 115-138 (1984).
Langer (1990) "New methods of drug delivery." Science 249:1527-1533.
Abuchowski et al. "Immunosuppressive properties and circulating life of Achromobacter glutaminase-asparaginase covalently attached to polyethylene glycol in man" Cancer Treat Rep. 65(11-12):1077-81. Nov.-Dec. 1981.
Katre et al. "Chemical modification of recombinant interleukin 2 by polyethylene glycol increases its potency in the murine Meth A sarcoma model" Proc Natl Acad Sci U S A. 84(6):1487-91. Mar. 1987.

* cited by examiner

*Primary Examiner* — D M Seaman
(74) *Attorney, Agent, or Firm* — Mark S. Cohen; Pearl Cohen Zedek Latzer Baratz LLP

(57) ABSTRACT

The invention relates to compositions and methods for treating various diseases or medical conditions by administering a methylxanthine compound. Specifically, the invention relates to compositions and methods for treating cytochrome oxidase (CcOX) mediated diseases or medical conditions by administering compositions comprising a methyl xanthine compound.

21 Claims, 6 Drawing Sheets

METHODS OF USING A METHYLXANTHINE COMPOUND

CROSS-REFERENCE TO RELATED APPLICATIONS

This application is a National Phase Application of PCT International Application PCT/US09/49086, filed Jun. 29, 2009, claiming priority to U.S. Patent Application 61/129,454, filed Jun. 27, 2008, which is incorporated by reference herein in its entirety.

CROSS REFERENCE TO RELATED APPLICATIONS

This application claims priority to U.S. provisional patent application 61/129,454, filed Jun. 27, 2008, which is incorporated herein by reference in its entirety.

GOVERNMENT INTEREST

This invention was made with government support under Grant Number K08 GM074117 awarded by National Institute of Health. The government has certain rights in the invention.

FIELD OF INVENTION

The invention relates to compositions and methods for treating various diseases or medical conditions by administering a methylxanthine compound. Specifically, the invention relates to treating cytochrome oxidase (CcOX) mediated diseases or medical conditions by administering compositions comprising a methylxanthine compound.

BACKGROUND OF THE INVENTION

Sepsis continues to be the major cause of death in critically ill patients and often results in multiple organ failure. Sepsis-associated myocardial dysfunction is often profound and can lead to refractory hypotension and cardiovascular collapse.

Altered mitochondrial function and impaired oxidative phosphorylation have been implicated in the development of sepsis-induced cardiac dysfunction and dysfunction in other organs Diminished function of any of the electron transport complexes could limit aerobic ATP synthesis and lead to bioenergetic failure. Cytochrome oxidase (CcOX), the terminal oxidase of the respiratory chain, uses electrons donated by cytochrome c to reduce oxygen to water. Coupled with the reduction of oxygen, CcOX pumps hydrogen ions across the mitochondrial inner membrane to the inter-membrane space. This creates and maintains a hydrogen ion gradient between the inside of the mitochondria and the inter-membrane space. This gradient generates the proton motive force that is crucial for ATP synthesis.

Myocardial CcOX is inhibited during sepsis. This inhibition is competitive and reversible early following cecal ligation and puncture (CLP, a well-established, well-accepted animal sepsis model that closely mimics human sepsis) and progresses becoming noncompetitive and irreversible during the late phase of sepsis. The onset of the hypodynamic phase and mortality in sepsis coincide with maximal competitive CcOX inhibition.

Accordingly, a need exists for improved methods and compositions for treating CcOX mediated diseases or medical conditions.

SUMMARY OF THE INVENTION

In one embodiment, the invention provides a method for treating a cytochrome oxidase (CcOX) mediated disease or medical condition, in a subject, the method comprising the step of administering to said subject a composition comprising a methylxanthine compound, thereby treating said CcOX mediated disease or medical condition. In one embodiment, the methylxanthine compound is caffeine.

In another embodiment, the invention provides a method for inhibiting or suppressing a cytochrome oxidase (CcOX) mediated disease or medical condition, in a subject, the method comprising the step of administering to said subject a composition comprising a methylxanthine compound, thereby inhibiting or suppressing said CcOX mediated disease or medical condition.

In another embodiment, the invention provides a method for reducing the symptoms associated with a cytochrome oxidase (CcOX) mediated disease or medical condition, in a subject, the method comprising the step of administering to said subject a composition comprising a methylxanthine compound, thereby reducing the symptoms associated with said CcOX mediated disease or medical condition.

In another embodiment, the invention provides a method for treating a subject afflicted with a sepsis associated myocardial dysfunction, the method comprising the step of administering to said subject a composition comprising a methylxanthine compound, thereby treating said subject afflicted with said sepsis associated myocardial depression.

In another embodiment, the invention provides a method for increasing the survival of a subject afflicted with a sepsis associated myocardial dysfunction, the method comprising the step of administering to said subject a composition comprising a methylxanthine compound, thereby increasing the survival of said subject afflicted with said sepsis associated myocardial depression.

In another embodiment, the invention provides a method for preventing sepsis associated myocardial dysfunction, in a subject, the method comprising the step of administering to said subject a composition comprising a methylxanthine compound, thereby preventing sepsis associated myocardial depression in said subject.

In another embodiment, the invention provides a method for reducing the symptoms associated with sepsis associated myocardial dysfunction, in a subject, the method comprising the step of administering to said subject a composition comprising a methylxanthine compound, thereby reducing the symptoms associated with sepsis associated myocardial depression in said subject.

In another embodiment, the invention provides a composition comprising a therapeutically effective amount of a methylxanthine compound to treat cytochrome oxidase (CcOX) mediated disease or disorder.

In another embodiment, the invention provides a composition comprising a therapeutically effective amount of caffeine to treat cytochrome oxidase (CcOX) mediated disease or disorder.

Other features and advantages of the present invention will become apparent from the following detailed description examples and figures. It should be understood, however, that the detailed description and the specific examples, while indicating preferred embodiments of the invention, are given by way of illustration only, since various changes and modifications within the spirit and scope of the invention will become apparent to those skilled in the art from this detailed description.

Figure 1:
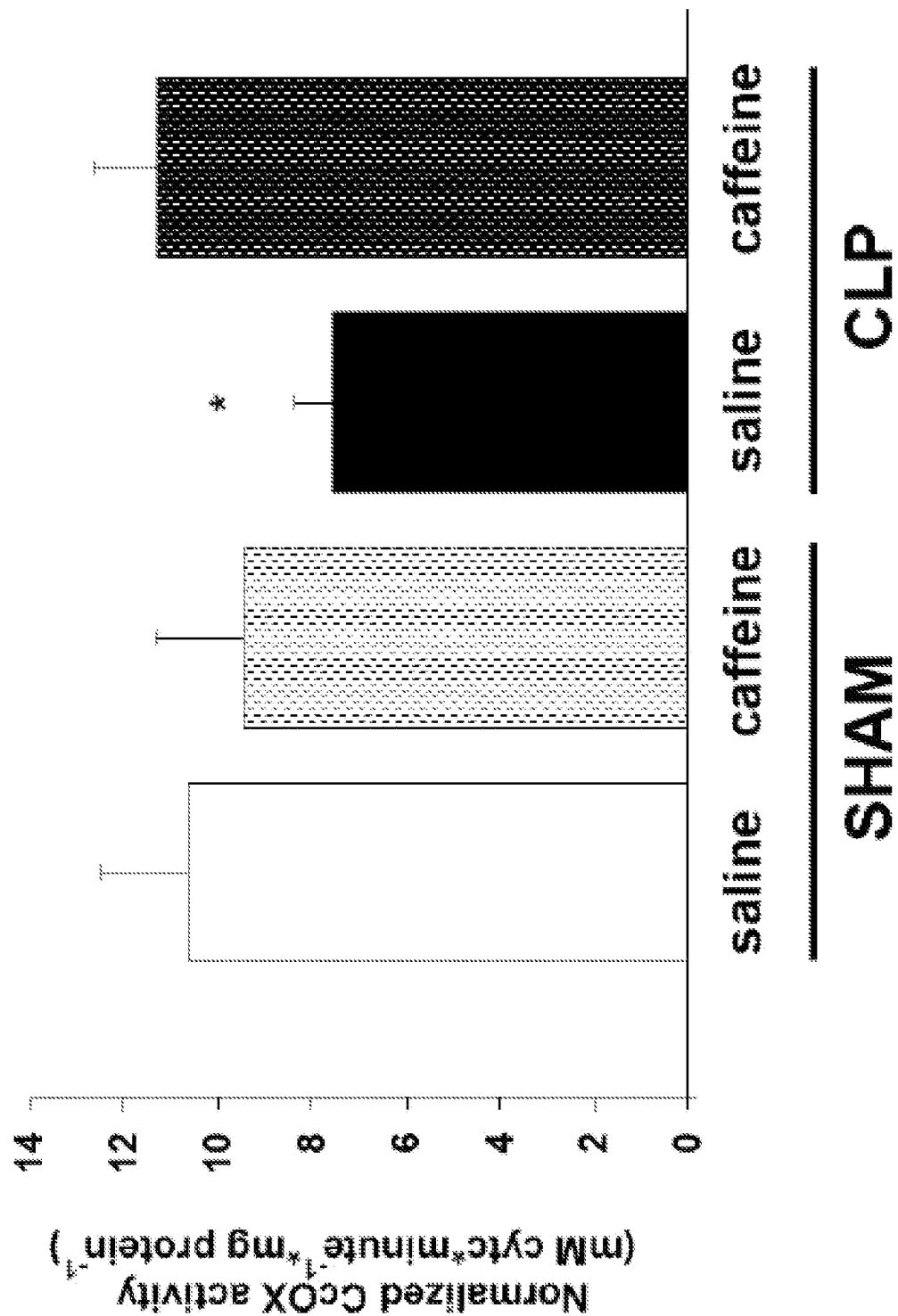
FIG. 1 shows myocardial CcOX kinetic activity. Steady-state cytochrome oxidase (CcOX) kinetic activity was measured in isolated mitochondria and normalized to citrate synthase activity. SHAM represents sham operated cohorts; CLP is cecal ligation and puncture, an animal model that closely mimics human sepsis. Saline and caffeine injected groups are presented. Values are expressed as means plus standard deviation. n=5 per group. *p<0.03 vs. SHAMsaline and CLP caffeine.

Survival was tracked to the 96-hour time point. SHAM represents sham operation, CLP represents cecal ligation and puncture. Saline injected (sal) and caffeine injected (caff) groups are demonstrated. Values represent percent survival. N=20 per group. *p<0.001 vs CLPsal, †p<0.01 vs SHAM groups.

DETAILED DESCRIPTION OF THE INVENTION

The invention is directed to compositions and methods for treating various diseases or medical conditions by administering a methylxanthine compound. Specifically, the invention is directed to treating cytochrome oxidase (CcOX) mediated diseases or medical conditions by administering compositions comprising a methyl xanthine compound.

In one embodiment, provided herein is a method for treating a cytochrome oxidase (CcOX) mediated disease or medical condition, in a subject, the method comprising the step of administering to said subject a composition comprising a methylxanthine compound, thereby treating said CcOX mediated disease or medical condition. In an exemplary embodiment, the methylxanthine compound is caffeine. In another embodiment, provided herein is a method for inhibiting or suppressing a CcOX mediated disease or medical condition, in a subject, the method comprising the step of administering to said subject a composition comprising a methylxanthine compound, thereby inhibiting or suppressing said CcOX mediated disease or medical condition. In another embodiment, provided herein is a method for reducing the symptoms associated with a CcOX mediated disease or medical condition, in a subject, the method comprising the step of administering to said subject a composition comprising a methylxanthine compound, thereby reducing the symptoms associated with said CcOX mediated disease or medical condition.

In another embodiment, provided herein is a method for treating a subject afflicted with a sepsis associated myocardial dysfunction, the method comprising the step of administering to said subject a composition comprising a methylxanthine compound, thereby treating said subject afflicted with said sepsis associated myocardial depression. In another embodiment, provided herein is a method for increasing the survival of a subject afflicted with a sepsis associated myocardial dysfunction, the method comprising the step of administering to said subject a composition comprising a methylxanthine compound, thereby increasing the survival of said subject afflicted with said sepsis associated myocardial depression.

In another embodiment, provided herein is a method for preventing sepsis associated myocardial dysfunction, in a subject, the method comprising the step of administering to said subject a composition comprising a methylxanthine compound, thereby preventing sepsis associated myocardial depression in said subject. In another embodiment, provided herein is a method for reducing the symptoms associated with sepsis associated myocardial dysfunction, in a subject, the method comprising the step of administering to said subject a composition comprising a methylxanthine compound, thereby reducing the symptoms associated with sepsis associated myocardial depression in said subject.

In one embodiment, provided are methods and compositions of treating various medical conditions by administering a methylxanthine compound. In other embodiments, provided are methods and compositions comprising caffeine for the treatment of sepsis and sepsis-induced cardiac dysfunction.

Examples of CcOX mediated disease or medical condition include, but are not limited to, a cardiac disease, sepsis, systemic inflammatory response syndrome, acute respiratory distress syndrome (ARDS), acute kidney injury (AKI), trauma, burn injury, hemorrhagic shock, a mitochondrial disorder, diseases that are characterized by a deficient cytochrome oxidase (CcOX) activity, and diseases that are characterized by a deficient mitochondrial function.

In one embodiment, provided herein is a method of treating a subject afflicted with a cardiac disease, sepsis, systemic inflammatory response syndrome, acute respiratory distress syndrome (ARDS), acute kidney injury (AKI), trauma, burn injury, hemorrhagic shock, a mitochondrial disorder, or any combination thereof, comprising the step administering to a subject a composition comprising a methylxanthine compound, thereby treating a subject afflicted with a cardiac disease, sepsis, systemic inflammatory response syndrome, acute respiratory distress syndrome (ARDS), acute kidney injury (AKI), trauma, burn injury, hemorrhagic shock, a mitochondrial disorder, or any combination thereof.

In another embodiment, provided herein is a method of treating a cardiac disease, sepsis, systemic inflammatory response syndrome, acute respiratory distress syndrome (ARDS), acute kidney injury (AKI), trauma, burn injury, hemorrhagic shock, a mitochondrial disorder, or any combination thereof in a subject, comprising the step administering to a subject a composition comprising methylxanthine compound, thereby restoring mitochondrial function to the subject.

The acute respiratory distress syndrome (ARDS) refers in one embodiment, to patients with an acute and progressive respiratory disease of a noncardiac nature, in association with diffuse bilateral pulmonary infiltrates demonstrated on chest radiograph, and with hypoxemia. In another embodiment, etiology of ARDS is classified as secondary lung injury following sepsis. Accordingly and in one embodiment, the methods and compositions provided herein are useful in the treatment of secondary ARDS.

In one embodiment, acute kidney injury (AKI), or acute tubular necrosis (ATN) refers to the entire spectrum of acute renal failure (ARF), a complex disorder that occurs in a wide variety of settings with clinical manifestations ranging from a minimal elevation in serum creatinine to anuric renal failure. In another embodiment, sepsis is a common cause of acute renal failure (ARF) and, despite extensive investigation, continues to have a high mortality. There have been few successful clinical trials although recent studies have shown that novel therapies targeting coagulation (activated protein C) and glucose control (intensive insulin therapy) can alter the prognosis of humans with sepsis. In one embodiment, the methods and compositions provided herein are useful in the treatment of AKI.

In another embodiment, provided herein a method of treating diseases that are characterized by a deficient mitochondrial function, comprising the step administering to a subject a composition comprising a methylxanthine compound, thereby restoring mitochondrial function to the subject. In another embodiment, diseases that are characterized by a deficient mitochondrial function are known to one of average skill in the art. In another embodiment, deficient mitochondrial function is characterized by a below normal cytochrome oxidase (CcOX) activity in a cell. In another embodiment, deficient mitochondrial function is characterized by a deficient cytochrome oxidase (CcOX) activity in a cell. In another embodiment, provided herein a method of treating diseases that are characterized by a deficient cytochrome oxidase (CcOX) activity in a cell, comprising the step of administering to a subject afflicted with a disease characterized by a deficient cytochrome oxidase (CcOX) activity in a cell a composition comprising methylxanthine compound. In another embodiment, provided herein a method of treating diseases that are characterized by a deficient cytochrome oxidase (CcOX) activity in a cell, comprising the step of administering to a subject afflicted with a disease characterized by a deficient cytochrome oxidase (CcOX) activity in a cell, a composition comprising caffeine.

In another embodiment, provided herein a method of preventing a cardiac disease, sepsis, systemic inflammatory response syndrome, acute respiratory distress syndrome, acute kidney injury, trauma, burn injury, hemorrhagic shock, a mitochondrial disorder, or any combination thereof in a subject, comprising the step of administering to a subject a composition comprising a methylxanthine compound, thereby preventing a cardiac disease, sepsis, systemic inflammatory response syndrome, acute respiratory distress syndrome, acute kidney injury, trauma, burn injury, hemorrhagic shock, a mitochondrial disorder, or any combination thereof in a subject.

In another embodiment, provided herein a method of preventing a cardiac disease, sepsis, systemic inflammatory response syndrome, acute respiratory distress syndrome, acute kidney injury, trauma, burn injury, hemorrhagic shock, a mitochondrial disorder, or any combination thereof in a subject, comprising the step of administering to a subject a composition comprising a methylxanthine compound, thereby reducing the risk of devoloping a cardiac disease, sepsis, systemic inflammatory response syndrome, acute respiratory distress syndrome, acute kidney injury, trauma, burn injury, hemorrhagic shock, a mitochondrial disorder, or any combination thereof in a subject.

In another embodiment, provided herein a method of preventing a cardiac disease, sepsis, systemic inflammatory response syndrome, acute respiratory distress syndrome, acute kidney injury, trauma, burn injury, hemorrhagic shock, a mitochondrial disorder, or any combination thereof in a subject, comprising the step of administering to a subject a composition comprising methylxanthine compound, thereby reducing the risk of developing aberrant mitochondrial function in a subject. In another embodiment, provided herein a method of preventing a cardiac disease, sepsis, systemic inflammatory response syndrome, acute respiratory distress syndrome, acute kidney injury, trauma, burn injury, hemorrhagic shock, a mitochondrial disorder, or any combination thereof in a subject, comprising the step of administering to a subject a composition comprising methylxanthine compound, thereby reducing the risk of developing reduced mitochondrial function in a subject.

In another embodiment, provided herein a method of preventing diseases that are characterized by a deficient mitochondrial function, comprising the step of administering to a subject a composition comprising methylxanthine compound, thereby restoring mitochondrial function to the subject. In another embodiment, provided herein a method of preventing diseases that are characterized by a deficient cytochrome oxidase (CcOX) activity in a cell, comprising the step of administering to a subject a composition comprising methylxanthine compound. In another embodiment, provided herein a method of preventing diseases that are characterized by a deficient cytochrome oxidase (CcOX) activity in a cell, comprising the step of administering to a subject in risk a composition comprising methylxanthine compound. In another embodiment, provided herein a method of preventing diseases that are characterized by a deficient cytochrome oxidase (CcOX) activity in a cell, comprising the step of administering to a subject a composition comprising caffeine.

In another embodiment, provided herein a method of reducing the symptoms associated with a cardiac disease, sepsis, systemic inflammatory response syndrome, acute respiratory distress syndrome, acute kidney injury, trauma, burn injury, hemorrhagic shock, a mitochondrial disorder, or any combination thereof in a subject, comprising the step of administering to a subject a composition comprising a methylxanthine compound, thereby reducing the symptoms associated with a cardiac disease, sepsis, systemic inflammatory response syndrome, acute respiratory distress syndrome, acute kidney injury, trauma, burn injury, hemorrhagic shock, a mitochondrial disorder, or any combination thereof in a subject. In some embodiments, sepsis and other diseases or conditions described herein are syndromes. In one embodiment, sepsis and other diseases or conditions described herein are syndromes comprising of multiple abnormalities.

In another embodiment, provided herein a method of reducing the symptoms associated with a cardiac disease, sepsis, systemic inflammatory response syndrome, acute respiratory distress syndrome, acute kidney injury, trauma, burn injury, hemorrhagic shock, a mitochondrial disorder, or any combination thereof in a subject, comprising the step of administering to a subject a composition comprising methylxanthine compound.

In another embodiment, provided herein a method of reducing the symptoms associated with diseases that are characterized by a deficient mitochondrial function, comprising the step of administering to a subject a composition comprising methylxanthine compound. In another embodiment, provided herein a method of reducing the symptoms associated with diseases that are characterized by a deficient cytochrome oxidase (CcOX) activity in a cell, comprising the step of administering to a subject a composition comprising methylxanthine compound. In another embodiment, provided herein a method of reducing the symptoms associated with diseases that are characterized by a deficient cytochrome oxidase (CcOX) activity in a cell, comprising the step of administering to a subject a composition comprising methylxanthine compound. In another embodiment, provided herein a method of reducing the symptoms associated with diseases that are characterized by a deficient cytochrome oxidase (CcOX) activity in a cell, comprising the step of administering to a subject a composition comprising caffeine.

In another embodiment, provided herein a method of treating a subject afflicted with a sepsis associated myocardial dysfunction, comprising the step of administering to a subject a composition comprising a methylxanthine compound.

In another embodiment, provided herein a method of treating a subject afflicted with a sepsis associated myocardial dysfunction, comprising the step of administering to a subject a composition comprising caffeine.

In another embodiment, provided herein a method of inducing cytochrome oxidase (CcOX) activity in a cell, comprising the step of contacting a cell with a composition comprising a methylxanthine compound. In another embodiment, provided herein a method of inducing cytochrome oxidase (CcOX) activity in a cardiac cell, comprising the step of contacting a cardiac cell with a composition comprising a methylxanthine compound.

In another embodiment, provided herein a method of increasing the survival of a subject afflicted with a sepsis associated myocardial dysfunction, comprising the step of administering to a subject a composition comprising caffeine.

In another embodiment, provided herein a method of preventing sepsis associated myocardial dysfunction in a subject, comprising the step of administering to a subject a composition comprising caffeine.

In another embodiment, provided herein a method of reducing the symptoms associated with sepsis and sepsis associated myocardial dysfunction in a subject, comprising the step of administering to a subject a composition comprising caffeine.

In another embodiment, diseases that are characterized by a deficient cytochrome oxidase (CcOX) activity in a cell include but are not limited to: metabolic disorders that affect tissues with high energy demands (brain, heart, muscle, liver, kidney).

In another embodiment, diseases that are characterized by a deficient cytochrome oxidase (CcOX) activity in a cell include diseases that are linked to mutations in nuclear-encoded proteins referred to as assembly factors, or assembly proteins. In another embodiment, diseases that are characterized by a deficient cytochrome oxidase (CcOX) activity in a cell include OXPHOS diseases. In another embodiment, diseases that are characterized by a deficient cytochrome oxidase (CcOX) activity in a cell include diseases that are linked to mutations in the following assembly factors: SURF1, SCO1, SCO2, COX10, COX15, and LRPPRC. In another embodiment, diseases that are characterized by a deficient cytochrome oxidase (CcOX) activity in a cell include Leigh syndrome, Alzheimer's disease, cardiomyopathy, leukodystrophy, anemia, and sensorineural deafness. In another embodiment, diseases that are characterized by a deficient cytochrome oxidase (CcOX) activity in a cell include Cyanide, sulfide, azide, or carbon monoxide poisoning.

In another embodiment, a methylxanthine compound restores mitochondrial function in a cell. In another embodiment, a methylxanthine compound restores mitochondrial function in a cardiac cell. In another embodiment, caffeine restores mitochondrial function in a cell. In another embodiment, caffeine restores mitochondrial function in a cardiac cell.

In another embodiment, a methylxanthine compound restores cytochrome oxidase (CcOX) activity in a cell. In another embodiment, a methylxanthine compound restores cytochrome oxidase (CcOX) activity in a cardiac cell. In another embodiment, caffeine restores cytochrome oxidase (CcOX) activity in a cell. In another embodiment, caffeine restores cytochrome oxidase (CcOX) activity in a cardiac cell.

In another embodiment, a methylxanthine compound increases cytochrome oxidase (CcOX) activity in a cell. In another embodiment, a methylxanthine compound increases cytochrome oxidase (CcOX) activity in a cardiac cell. In another embodiment, caffeine increases cytochrome oxidase (CcOX) activity in a cell. In another embodiment, caffeine increases cytochrome oxidase (CcOX) activity in a cardiac cell.

In another embodiment, a methylxanthine compound increases left ventricular pressure (LVP) in the heart in a subject. In another embodiment, caffeine increases left ventricular pressure (LVP) in the heart in a subject.

In another embodiment, a methylxanthine compound increases left ventricular pressure (LVP) in the heart in a subject afflicted with a disease characterized by a deficient mitochondrial function. In another embodiment, a methylxanthine compound increases left ventricular pressure (LVP) in the heart in a subject afflicted with a disease characterized by a deficient cytochrome oxidase (CcOX) activity in a cell. In another embodiment, a methylxanthine compound increases left ventricular pressure (LVP) in the heart in a subject afflicted with a disease characterized by a deficient cytochrome oxidase (CcOX) activity in a cardiac cell. In another embodiment, a methylxanthine compound maintains left ventricular pressure (LVP) in the heart in a subject afflicted with a disease characterized by a deficient mitochondrial function.

In another embodiment, caffeine increases left ventricular pressure (LVP) in the heart in a subject afflicted with a disease characterized by a deficient mitochondrial function. In another embodiment, caffeine increases left ventricular pressure (LVP) in the heart in a subject afflicted with a disease characterized by a deficient cytochrome oxidase (CcOX) activity in a cell. In another embodiment, caffeine increases left ventricular pressure (LVP) in the heart in a subject afflicted with a disease characterized by a deficient cytochrome oxidase (CcOX) activity in a cardiac cell. In another embodiment, caffeine maintains left ventricular pressure (LVP) in the heart in a subject afflicted with a disease characterized by a deficient cytochrome oxidase (CcOX) activity in a cardiac cell.

In another embodiment, LVP-volume loops are a useful measure of left ventricular (LV) performance in a relatively load-independent manner. In another embodiment, loops acquired with an LV conductance and LV pressure catheters are similar under various conditions to those acquired with echocardiographic automated border detection and LV pressure.

In another embodiment, a methylxanthine compound increases the pressure developed during isovolumic contraction and relaxation in the heart in a subject. In another embodiment, caffeine increases the pressure developed during isovolumic contraction and relaxation in the heart in a subject.

In another embodiment, a methylxanthine compound increases isovolumic contraction and relaxation in the heart in a subject afflicted with a disease characterized by a deficient mitochondrial function. In another embodiment, a methylxanthine compound increases isovolumic contraction and relaxation in the heart in a subject afflicted with a disease characterized by a deficient cytochrome oxidase (CcOX) activity in a cell. In another embodiment, a methylxanthine compound increases isovolumic contraction and relaxation in the heart in a subject afflicted with a disease characterized by a deficient cytochrome oxidase (CcOX) activity in a cardiac cell.

In another embodiment, caffeine increases isovolumic contraction and relaxation in the heart in a subject afflicted with a disease characterized by a deficient mitochondrial function. In another embodiment, caffeine increases isovolumic contraction and relaxation in the heart in a subject afflicted with a disease characterized by a deficient cytochrome oxidase (CcOX) activity in a cell. In another embodiment, caffeine increases isovolumic contraction and relaxation in the heart in a subject afflicted with a disease characterized by a deficient cytochrome oxidase (CcOX) activity in a cardiac cell.

In another embodiment, isovolumic indexes are more robust. In another embodiment, correlation exists between peak velocity during isovolumic contraction and ejection fraction. In another embodiment, peak endocardial acceleration occurs during isovolumic contraction and increases linearly during dobutamine infusion. In another embodiment, myocardial acceleration during isovolumic contraction (IVA) is a relatively load-independent index of left ventricular (LV) contractile function.

In another embodiment, the invention provides a composition comprising a therapeutically effective amount of a methylxanthine compound to treat cytochrome oxidase (CcOX) mediated disease or disorder. A "therapeutically effective amount" refers to an amount effective, at dosages and for periods of time necessary, to achieve the desired therapeutic result. A therapeutically effective amount of the compound may vary according to factors such as the disease state, age, sex, and weight of the individual, and the ability of the compound to elicit a desired response in the individual. A therapeutically effective amount is also one in which any toxic or detrimental effects of the compound are outweighed by the therapeutically beneficial effects.

Examples of a methylxanthine compound includes methylated derivatives of xanthine, for example, but are not limited to caffeine, theobromine and theophylline.

In another embodiment, the invention provides a composition comprising a therapeutically effective amount of caffeine to treat cytochrome oxidase (CcOX) mediated disease or disorder. In another embodiment, the invention provides a composition comprising a therapeutically effective amount of theobromine to treat cytochrome oxidase (CcOX) mediated disease or disorder. In another embodiment, the invention provides a composition comprising a therapeutically effective amount of theophylline to treat cytochrome oxidase (CcOX) mediated disease or disorder.

Dosage regimens may be adjusted to provide the optimum desired response (e.g., a therapeutic or prophylactic response). In one example, a single bolus may be administered. In another example, several divided doses may be administered over time. In yet another example, the dose may be proportionally reduced or increased as indicated by the exigencies of the therapeutic situation. Dosage unit form, as used herein, refers to physically discrete units suited as unitary dosages for treating mammalian subjects. Each unit may contain a predetermined quantity of active compound calculated to produce a desired therapeutic effect. In some embodiments, the dosage unit forms of the invention are dictated by and directly dependent on the unique characteristics of the active compound and the particular therapeutic or prophylactic effect to be achieved, in association with the required pharmaceutical carrier.

In another embodiment, a daily dose of about 0.5-20 mg/kg caffeine is administered to a subject in need according to the method as described herein. In another embodiment, a daily dose of about 0.5-15 mg/kg caffeine is administered to a subject in need according to the method as described herein. In another embodiment, a daily dose of about 1-15 mg/kg caffeine is administered to a subject in need according to the method as described herein. In another embodiment, a daily dose of about 1-10 mg/kg caffeine is administered to a subject in need according to the method as described herein. In another embodiment, a daily dose of about 2-8 mg/kg caffeine is administered to a subject in need according to the method as described herein. In another embodiment, a daily dose of about 8-20 mg/kg caffeine is administered to a subject in need according to the method as described herein. In another embodiment, a daily dose of about 10-20 mg/kg caffeine is administered to a subject in need according to the method as described herein. In another embodiment, a daily dose of about 7-15 mg/kg caffeine is administered to a subject in need according to the method as described herein.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In another embodiment, the daily dose of caffeine is administered once a day. In another embodiment, the daily dose of caffeine is administered twice a day. In another embodiment, the daily dose of caffeine is administered three times a day. In another embodiment, the daily dose of caffeine is administered four times a day. In another embodiment, the daily dose of caffeine is administered five times a day. In another embodiment, the daily dose of caffeine is administered six times a day. In another embodiment, the caffeine is administered by continuous infusion over a period, for example 24 hour period.

In another embodiment, the invention further provides compositions comprising caffeine and additionally one or more active pharmaceutical ingredient.

In another embodiment, caffeine is extracted using supercritical carbon. In another embodiment, caffeine is extracted using nonhazardous organic solvents. In another embodiment, caffeine is extracted using ethyl acetate. In another embodiment, caffeine is extracted using ethanol. In another embodiment, caffeine is extracted using acetic acid.

In another embodiment, caffeine is administered in a tablet. In another embodiment, caffeine is administered in a capsule. In another embodiment, caffeine is administered in a chewable oral formulation. In another embodiment, caffeine is administered in a liquid oral formulation. In another embodiment, caffeine is administered in a NoDoz, maximum strength; Vivarin tablet. In another embodiment, caffeine is administered in an Excedrin tablet. In another embodiment, caffeine is administered in an Anacin tablet. In another embodiment, caffeine is administered in a beverage. In another embodiment, caffeine is administered in coffee. In another embodiment, caffeine is administered in tea. In another embodiment, caffeine is administered in coffee. In another embodiment, caffeine is administered in caffeinated waters. In another embodiment, caffeine is administered in coffee. In another embodiment, caffeine is administered in Java water. In another embodiment, caffeine is administered in a caffeinated dissert. In another embodiment, caffeine is administered in a caffeinated ice cream. In another embodiment, caffeine is administered in a chocolate.

The caffeine of the present invention and pharmaceutical compositions comprising same can be, in another embodiment, administered to a subject by any method known to a person skilled in the art, such as parenterally, paracancerally, transmucosally, transdermally, intramuscularly, intravenously, intra-dermally, subcutaneously, intra-peritonealy, intra-ventricularly, intra-cranially, intra-vaginally or intra-tumorally.

In another embodiment of methods and compositions of the present invention, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound (e.g. the mimetic compound, peptide or nucleotide molecule) and the inert carrier or diluent, a hard gelating capsule.

In another embodiment, the pharmaceutical compositions are administered by intravenous, intra-arterial, or intra-muscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, the pharmaceutical composition is administered as a suppository, for example a rectal suppository or a urethral suppository. In another embodiment, the pharmaceutical composition is administered by subcutaneous implantation of a pellet. In another embodiment, the pellet provides for controlled release of active agent over a period of time.

In other embodiments, carriers or diluents used in methods of the present invention include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In another embodiment, parenteral vehicles (for subcutaneous, intravenous, intra-arterial, or intramuscular injection) include sodium chloride solution, Ringer's dextrose, dextrose and sodium chloride, dextrose and water, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In other embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCI., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants. Each of the above excipients represents a separate embodiment of the present invention.

In another embodiment, the pharmaceutical compositions provided herein are controlled-release compositions, i.e. compositions in which the active compound is released over a period of time after administration. Controlled- or sustained-release compositions include formulation in lipophilic depots (e.g. fatty acids, waxes, oils). In another embodiment, the composition is an immediate-release composition, i.e. a composition in which of the active compound is released immediately after administration.

In another embodiment, the pharmaceutical composition is delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials are used; e.g. in microspheres in or an implant. In yet another embodiment, a controlled release system is placed in proximity to the target cell, thus requiring only a fraction of the systemic dose (see, e.g., Goodson, in Medical Applications of Controlled Release, supra, vol. 2, pp. 115-138 (1984); and Langer R, Science 249: 1527-1533 (1990).

The compositions also include, in another embodiment, incorporation of the active material into or onto particulate preparations of polymeric compounds such as polylactic acid, polglycolic acid, hydrogels, etc.

Also included in the present invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compounds solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

Each of the above additives, excipients, formulations and methods of administration represents a separate embodiment of the present invention.

The methylxanthine compound may be administered alone (monotherapy), or in combination with one or more therapeutically effective agents or treatments (combination therapy). The other therapeutically effective agent may be conjugated to the compound, incorporated into the same composition as the compound, or may be administered as a separate composition. The other therapeutically agent or treatment may be administered prior to, during and/or after the administration of the compound. The other therapeutically effective agent may be administered to augment the therapeutic effect of the compound, or to diminish the negative side effects of the compound.

As used herein, the terms "treat" and "treatment" refer to therapeutic treatment, wherein the object is to prevent or slow down (lessen) an undesired physiological change associated with a disease, syndrome or disorder. Beneficial or desired clinical results include alleviation of symptoms, diminishment of the extent of a disease or disorder, stabilization of a disease or disorder (i.e., where the disease or disorder does not worsen), delay or slowing of the progression of a disease, syndrome or disorder, amelioration or palliation of the disease, syndrome or disorder, and remission (whether partial or total) of the disease, syndrome or disorder, whether detectable or undetectable. "Treatment" can also mean prolonging survival as compared to expected survival if not receiving treatment. Those in need of treatment include those already with the disease, syndrome or disorder as well as those prone to having the disease or disorder.

The term "about" as used herein means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

The following examples are presented in order to more fully illustrate the preferred embodiments of the invention. They should in no way be construed, however, as limiting the broad scope of the invention.

EXAMPLES

Materials and Experimental Methods

Test Animals

The care of the animals in this study was in accordance with NIH and Institutional Animal Care and Use Committee guidelines. Under isoflurane general anesthesia (up to 2%), 250 g male Sprague-Dawley rats (Charles River, Boston, Mass., USA) underwent cecal ligation and double puncture (CLP) with an 18-gauge needle or sham operation as previously described. All animals were administered 50 ml/kg saline subcutaneously immediately post procedure and every 24 hours. Once awake, animals were given access to food and water ad libitum.

Caffeine Injection

Twenty four and 48 hours post-procedure, rats received either an intraperitoneal (i.p) injection of caffeine (7.5 mg/kg, Sigma-Aldrich, St. Louis, Mo.) or equal volume saline (1 mL). Rats were sacrificed one hour after the 48 hour injection following euthanasia with 150 mg/kg of intraperitoneal pentobarbital. Four cohorts were evaluated: SHAM saline, SHAM caffeine, CLP saline, CLP caffeine. N=5 per group. The 24-hour time point was chosen for initial intervention based on the onset of the hypodynamic phase when cardiac function begins to deteriorate and the presence of reversible CcOX inhibition. Studies were performed at the 48-hour time point because this time point represents the late phase of sepsis when cardiac function is markedly depressed and mortality is 75%.

Mitochondrial Isolation

Cardiac ventricles were harvested and homogenized in ice-cold H medium (70 mM sucrose, 220 mM mannitol, 2.5 mM Hepes, pH 7.4 and 2 mM EDTA). The homogenate was spun at 1500×g for 10 min at 4° C. Supernatants were removed and centrifuged at 10,000×g for 10 mM at 4° C. Pellets were resuspended in H medium and centrifuged again at 10,000×g for 10 min at 4° C. Pellets were again resuspended in H medium and mitochondrial protein concentration determined using the method of Lowry.

Cytochrome Oxidase Steady-state Kinetics

CcOX kinetics were assayed by the method of Smith in which the rate of oxidation of ferrocytochrome c was measured by following the decrease in absorbance at 550 nm. Assays were executed in a 1-mL reaction volume containing 50 mM $PO4^{-2}$ (pH 7.0), 2% lauryl maltoside, and 1 μg of mitochondrial protein. Ferrocytochrome c was added at a concentration of 40 mM to initiate the reaction. Specific activity was calculated from mean values of three to four measurements using 21.1 $mM \cdot cm^{-1}$ as the extinction coefficient of ferrocytochrome c at 550 nm.

Citrate synthase activity was measured via spectrophotometry based on the change in absorbance at 412 nm induced by the cleavage of the thiol ester bond of acetyl-CoA and the utilization of oxaloacetate (Sigma-Aldrich, St. Louis, Mo.). CcOX activities were normalized to citrate synthase activities Steady-state Levels of Cardiac Cytochrome Oxidase Subunit I (The Active Site)

10 μg samples of mitochondrial protein were subjected to SDS-acrylamide gel electrophoresis and immunoblotting. Blots were labeled with a primary polyclonal antibody to mouse CcOX I (Molecular Probes, Eugene, Oreg., USA) and secondarily exposed to rabbit anti-mouse IgG (Santa Cruz Biotechnology Inc., Santa Cruz, Calif.). Mitochondrial protein loading was assessed with a primary monoclonal antibody to mouse porin (VDAC, Molecular Probes, Eugene, Oreg., USA) and secondarily exposed to rabbit anti-mouse IgG (Santa Cruz Biotechnology Inc., Santa Cruz, Calif.). The signal was detected with enhanced chemiluminescence (ECL; Amersham Pharmacia Biotech, Piscataway, N.J., USA), and density was measured using scanning densitometry. Five animals per group per experiment were evaluated.

Isolated Rat Heart Preparation

Rats were anesthetized with intraperitoneal pentobarbital (70 mg/kg) and heparinized (1000 U IP). The heart was excised rapidly and the aorta was cannulated. Retrograde perfusion was initiated at constant flow (12 mL/g-min) with a modified Krebs-Henseleit buffer containing (mmol/L) NaCl 120, KCl 4.7, $MgSO_4$ 1.2, $KH_2PO_4$ 1.2, $CaCl_2$ 1.25, $NaHCO_3$ 25, and glucose. The non-recirculating buffer was maintained at pH 7.4 equilibrated with 95% $O_2$-5% $CO_2$ at 37° C. Isovolumetric left ventricle pressure (LVP) was measured with a transducer connected to a saline-filled latex balloon inserted into the left ventricle through the left atrium. The balloon was inflated to maintain an end-diastolic pressure of 10 mmHg Hearts were immersed in a water-jacketed chamber maintained at 37° C. and allowed to stabilize for 30 minutes.

Heart rate, LVP, the maximum rate of positive and negative change in LVP (+/−dP/dt), and aortic pressure were collected with an analog-to-digital converter system (Power Laboratory 4SP, ADInstruments, Castle Hill, Australia). All variables were displayed and recorded (Chart ver. 4.12, ADInstruments). Measurements were obtained at coronary flow rates (CF) of 12, 10, 8, 6, and 4 mL/g-min Coronary inflow oxygen tension ($PaO_2$) and coronary sinus oxygen tension (PvO2) were measured (GEM Premier 3000, Instrumentation Laboratory, Belgium). Percent O2 extraction was calculated as $100 \times (PaO_2-PvO_2/PaO_2)$. Myocardial $O_2$ consumption ($MO_2$) was calculated as $CF/g \times (PaO_2-PvO_2) \times O_2$ solubility at 760 mmHg $O_2$ solubility is 24 |il/ml $H_2O$ at 37° C. Coronary perfusion pressure was calculated as the difference between mean aortic pressure and LV end-diastolic pressure. Coronary resistance was calculated by dividing perfusion pressure by coronary flow.

Survival

The survival was followed in a separate cohort of animals in this two treatment parallel-design study to 96 hours. Each animal was injected with either caffeine (7.5 mg/kg i.p.) or equal volume of saline (1 mL i.p.) every 24 hours beginning 24 hours following CLP or sham operation. Twenty animals per group were evaluated based on the probability being 80 percent that the study will detect a treatment difference at a two-sided 5.0 percent significance level, if the true hazard ratio is 3.

Statistics

Data are presented as mean +/− standard deviation. Statistical significance was assessed using ANOVA and post hoc Tukey's test with $p<0.05$. Statistical significance in the survival study was assessed using Kaplan-Meier survival curves and Mantel-Cox log-rank test.

Example 1

Caffeine Overcomes CcOX Inhibition and Restores CcOX Kinetic Activity

Myocardial CcOX activity was measured via spectrophotometry in isolated mitochondria and normalized to citrate synthase activity. Consistent with prior findings, normalized myocardial CcOX activity significantly decreased 48 hours following CLP in rats that received saline injection (FIG. 1). Caffeine injection, however, restored CcOX kinetic activity in CLP rats to sham values (FIG. 1). There was no significant difference in CcOX activity between saline injected and caffeine injected sham animals (FIG. 1).

Example 2

Steady-State Levels of Myocardial CcOX-I are Unchanged Following CLP

Figure 2:
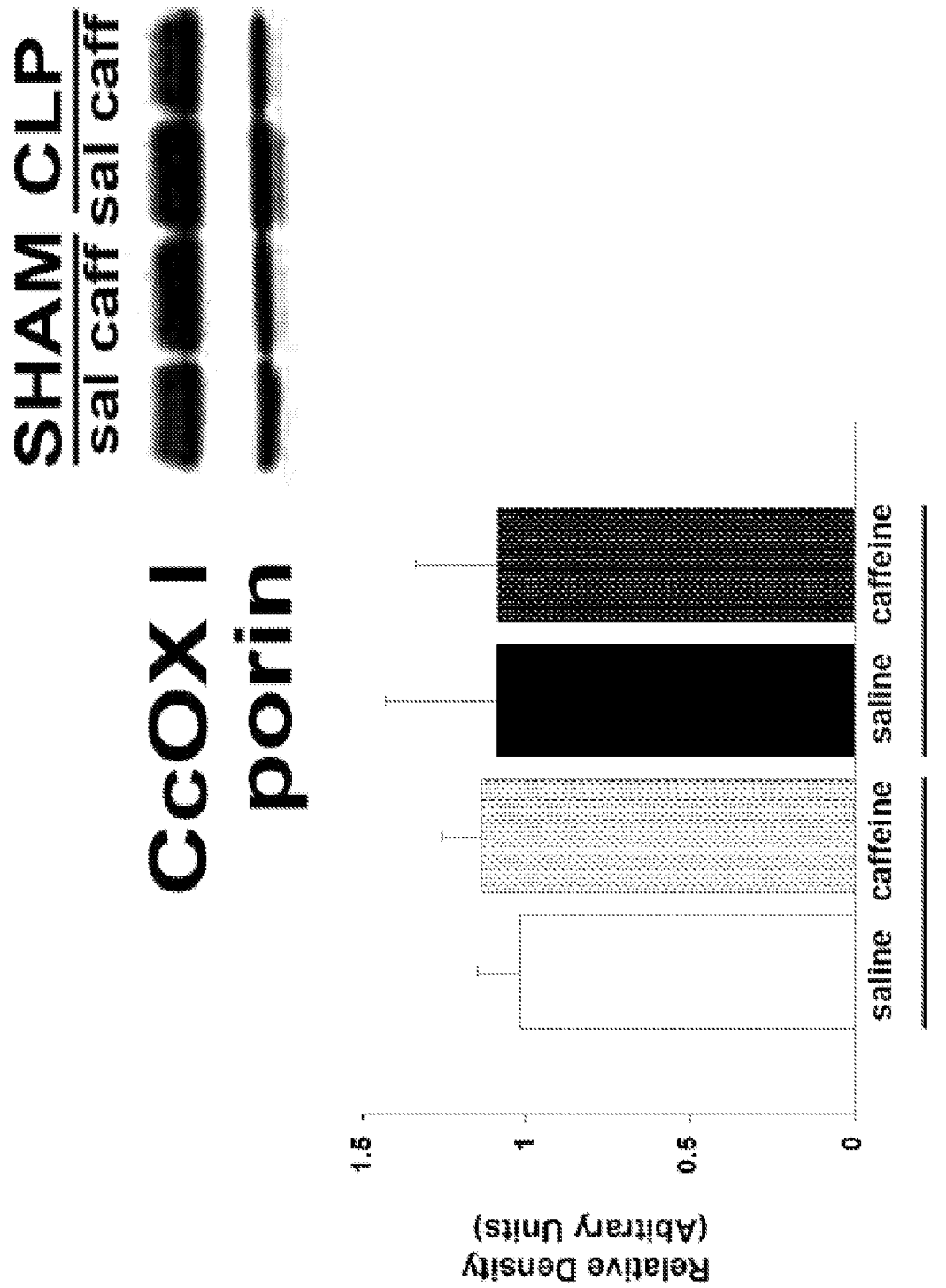
FIG. 2 shows steady state levels of CcOX-I protein. An autoradiogram of a representative immunoblot of cytochrome oxidase subunit I (CcOX-I) is depicted. SHAM represents sham operation, CLP represents cecal ligation and puncture. Saline injected (sal) and caffeine injected (caff) groups are demonstrated. Porin was used as the mitochondrial protein loading control. Graphical representation of relative densities shown below the blot. Values were derived by calculating the means and standard deviations of data from five animals in each group. These data are normalized to porin. Sham saline values were set arbitrarily to 1. n=5 per group. p=NS.

Immunoblot analysis for CcOX subunit I (the active site) was performed. There was no significant difference in steady-state myocardial CcOX I levels between all groups (FIG. 2). Thus, change in CcOX activity following CLP in saline injected animals was not on the basis of changes in enzyme levels.

Example 3

Caffeine Improves Cardiac Dysfunction

To assess the effect of caffeine on cardiac function, an isolated rat heart preparation was used and heart rate, LVP, and the maximum rate of positive and negative change in LVP (+/−dP/dt) were measured over a range of coronary flow rates. There was no significant difference in heart rate between groups (263+/−30 bpm, sham saline; 276+/−11 bpm, sham caffeine; 260+/−17 bpm, CLP saline; 262+/−11 bpm CLP caffeine; p=NS).

Figure 3:
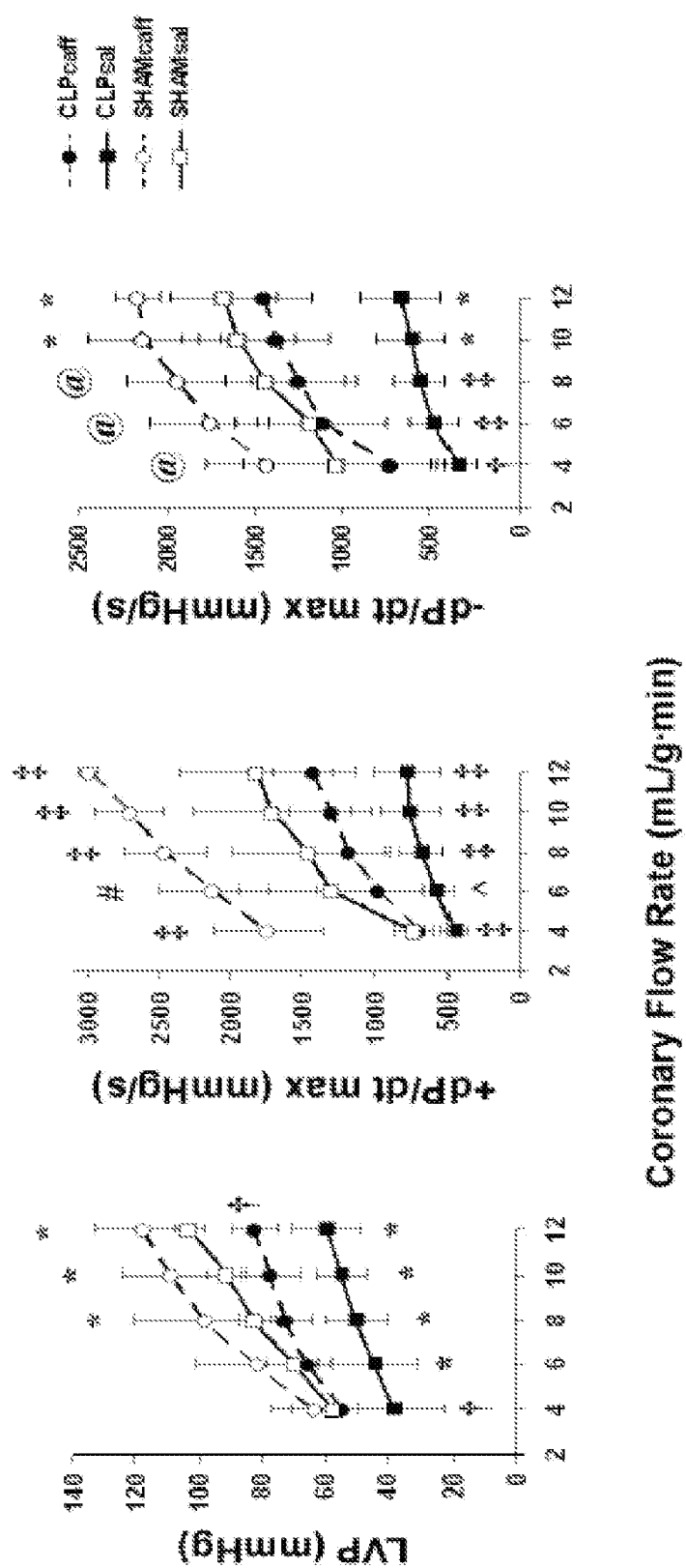
FIG. 3 shows left ventricular function. Left ventricular developed pressure (LVP) and the maximum rate of positive and negative change in LVP (+/−dP/dt) were measured over a range of coronary flow rates using an isolated rat heart preparation. SHAM represents sham operation; CLP represents cecal ligation and puncture. Saline injected (sal) and caffeine injected (caff) groups are demonstrated. Values are expressed as means +/−standard deviation. n=5 per group. *p<0.01 vs all other groups, ‡p<0.05 vs all other groups, †P<0.05 vs SHAM groups, @p<0.05 vs CLP groups, #p<0.05 vs CLPsal, ^p<0.01 vs SHAMcaff.

However, CLP induced significant reductions in LVP in saline injected animals across all coronary flow rates compared to both sham cohorts (FIG. 3). Caffeine significantly improved LVP following CLP compared to saline injection at all flow rates greater than 4 mL/g-min (FIG. 3). LVP in caffeine injected CLP animals approached saline injected sham values except at 12 mL/g-min coronary flow where it was significantly lower than both sham cohorts (FIG. 3). Interestingly, caffeine significantly increased LVP in sham operated animals compared to all other groups at the highest coronary flow rates (FIG. 3).

As with LVP, CLP caused significant reductions in dP/dt in saline injected animals (FIG. 3). Compared to both sham cohorts, saline injected CLP significantly decreased +dP/dt at the majority of coronary flow rates and decreased −dP/dt at all flow rates (FIG. 3). Caffeine significantly improved both +dP/dt and −dP/dt following CLP toward saline injected sham values at most flow rates (FIG. 3). Again, caffeine significantly increased +dP/dt and −dP/dt following sham operation compared to both CLP groups at all coronary flow rates and significantly increased +dP/dt and −dP/dt compared to saline injected sham values at the highest flow rates (FIG. 3).

Figure 4:
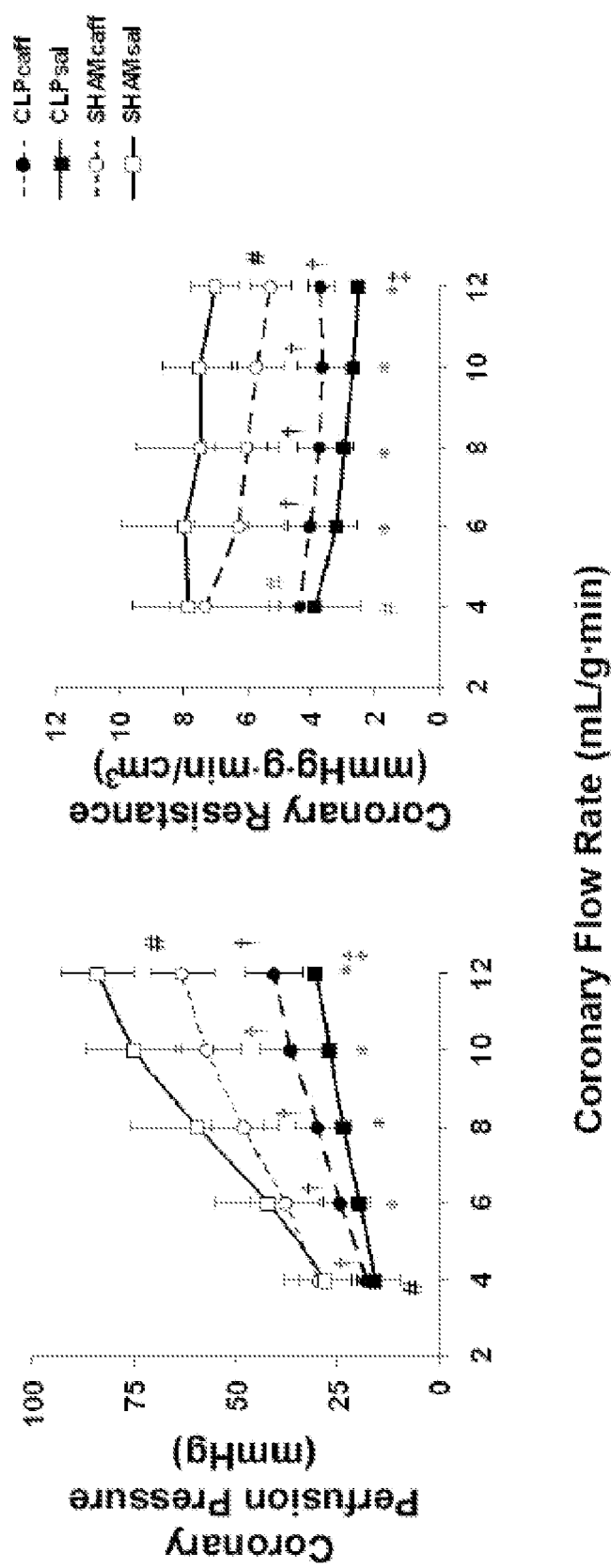
FIG. 4 shows coronary artery perfusion pressure and resistance. Perfusion pressure was measured over a range of coronary flow rates using an isolated rat heart preparation. Resistance was calculated by dividing perfusion pressure by flow. SHAM represents sham operation, CLP represents cecal ligation and puncture. Saline injected (sal) and caffeine injected (caff) groups are demonstrated. Values are expressed as means +/−standard deviation. n=5 per group. *p<0.05 vs SHAM groups, ‡p<0.05 vs CLPcaff, †p<0.05 vs SHAM groups, #p<0.05 vs SHAMsal.

With regard to coronary perfusion pressure, CLP caused significant reductions in both saline and caffeine injected cohorts compared to sham controls at almost all coronary flow rates (FIG. 4). Compared to saline injected CLP, caffeine injection significantly increased coronary perfusion pressure at 12 mL/g-min of coronary flow (FIG. 4). Interestingly, caffeine injection significantly reduced coronary perfusion pressure at the highest flow rate following sham operation compared to saline injection (FIG. 4). Similar changes were seen with regard to coronary resistance (FIG. 4).

Caffeine injection significantly increased coronary resistance following CLP and significantly decreased resistance following sham operation compared to their saline injection counterparts, respectively suggesting alternative mechanisms (FIG. 4). Significant reductions in resistance in both CLP groups were consistent with sepsis-induced vasodilation.

Figure 5:
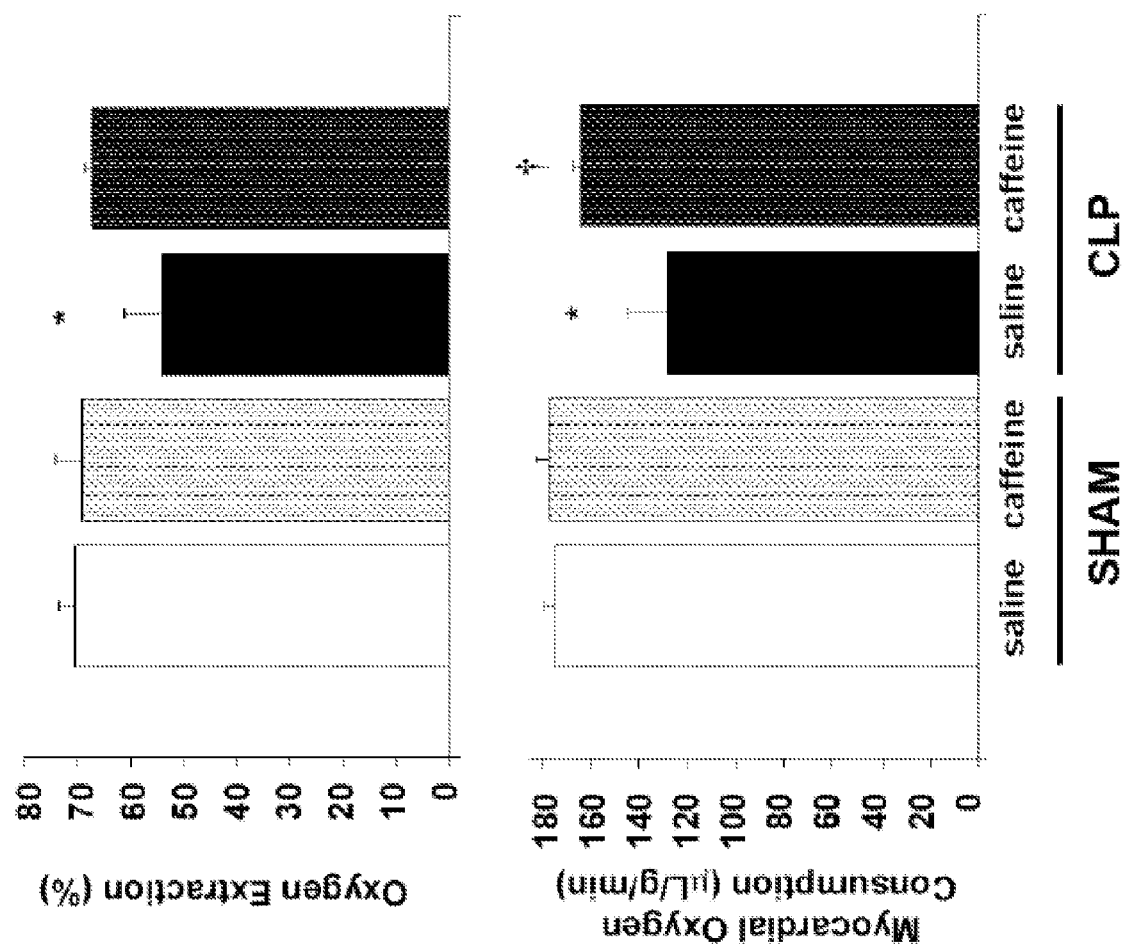
FIG. 5 shows myocardial oxygen extraction and consumption in situ. Percent O2 extraction and myocardial oxygen consumption were calculated from the difference between coronary inflow oxygen tension (PaO2) and coronary sinus oxygen tension (PvO2) in an isolated heart preparation. SHAM represents sham operation, CLP represents cecal ligation and puncture. Saline and caffeine injected groups are presented. Values are expressed as means plus standard deviation. n=5 per group. *p<0.04 vs all groups, †p<0.04 vs SHAMcaffeine.

To assess in situ mitochondrial function, myocardial oxygen extraction and oxygen consumption were measured at 12 mL/g-min coronary flow following stabilization. Consistent with CcOX inhibition, both oxygen extraction and consumption significantly decreased following CLP in saline injected animals compared to all groups (FIG. 5A, 5B). Caffeine, however, significantly increased both oxygen extraction and consumption following CLP compared to saline injected sham values (FIG. 5A, 5B). Following sham operation, caffeine significantly increased myocardial oxygen consumption compared to both CLP cohorts (FIG. 5B).

Example 4

Caffeine Enhances Survival Following CLP

Figure 6:
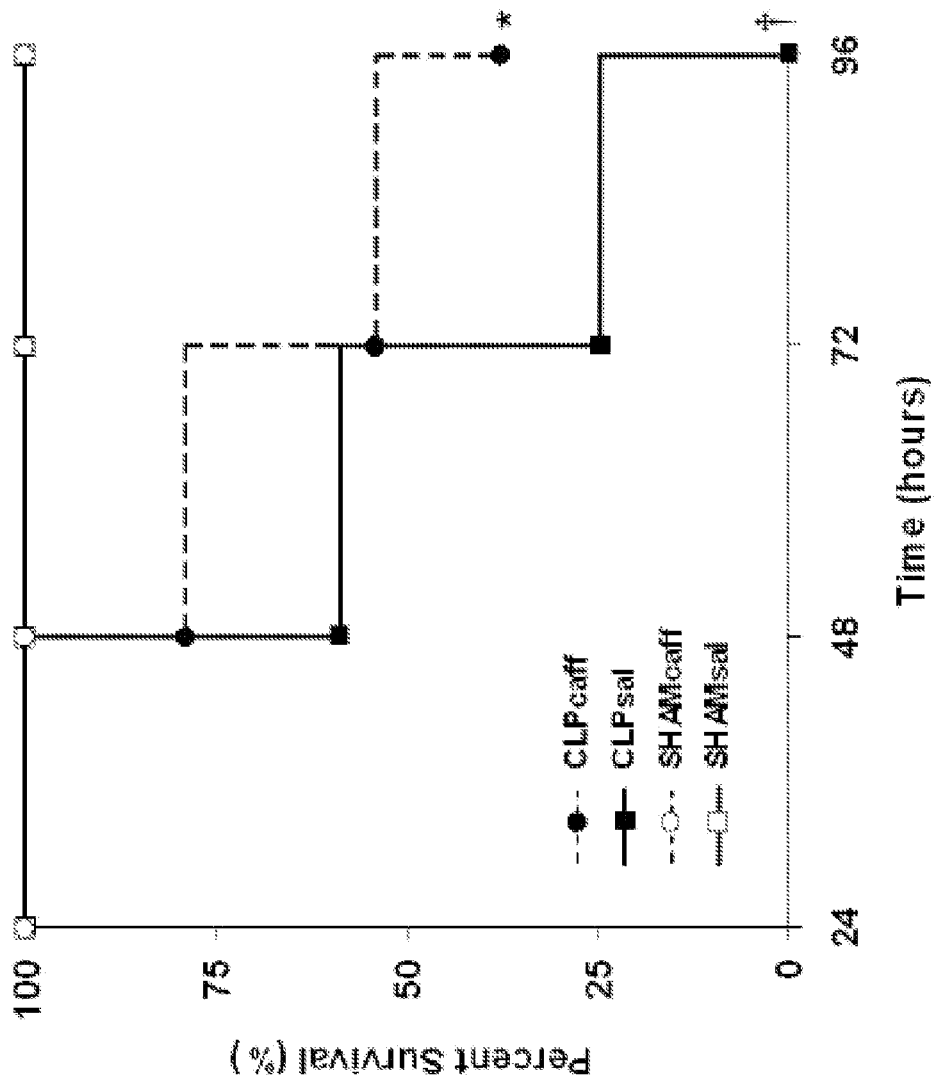
FIG. 6 shows Kaplan-Meier survival curves. Animals were either injected with intraperitoneal caffeine or an equal volume of saline at the 24-hour time point and every 24 hours.

In order to assess the effect of caffeine on sepsis-induced mortality, survival was tracked in a separate cohort of animals receiving either a daily injection of caffeine or equal volume of saline. Following CLP, 60% of saline injected animals survived to 48 hours, 25% survived to 72 hours, and none survived to 96 hours post procedure (FIG. 6). On the other hand, caffeine injection significantly improved survival post CLP. Eighty percent of caffeine injected animals survived to 48 hours, 55% survived to 72 hours, and 40% survived to 96 hours post CLP (FIG. 6). There was no mortality observed in either sham cohort (FIG. 6).

A daily injection of caffeine beginning 24 hours post CLP (roughly equivalent to the human consumption of a single cup of coffee) restored CcOX function to sham values at 48 hours. Increased oxygen extraction and myocardial oxygen consumption in the isolated rat heart preparation corroborated this finding in situ. These data strongly suggest that caffeine stimulated oxidative phosphorylation during sepsis and were associated with significant improvements cardiac function and survival.

It is important to note that, despite caffeine-induced restoration of CcOX function following CLP, LVP was significantly less than sham values at the highest coronary flow rate. In addition, although caffeine considerably improved survival to 96 hours post CLP, mortality remained significantly high. This may be explained a number of ways. First, depressed LVP in the setting of restored oxygen consumption suggests that caffeine may have potentially uncoupled oxidative phosphorylation. In other words, electron transport and oxygen consumption were dissociated from ATP production. Therefore, bioenergetic capacity would not be restored entirely and limited ATP synthesis could continue to impair cardiac function. Another explanation is the multifactorial nature of sepsis. It is very likely that impaired CcOX activity by itself is not solely responsible for sepsis-induced organ failure. Thus, abrogation of myocardial CcOX inhibition during sepsis may not completely restore cardiac function. In addition, cardiac dysfunction likely contributes to sepsis-induced mortality but may not be the sole cause it. Thus, marked improvement in myocardial function may not necessarily equate with marked improvements in survival.

These results demonstrate that caffeine, given in a dose equivalent to the average daily human consumption, results in restoration of myocardial CcOX activity, improved cardiac function, and enhanced survival during sepsis.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method of treating a subject afflicted with sepsis-associated myocardial depression, comprising the step administering to said subject a composition comprising a therapeutically effective amount of a methylxanthine compound.

2. The method of claim 1, whereby said methylxanthine compound is caffeine.

3. The method of claim 1, whereby said methylxanthine compound increases cytochrome oxidase (CcOX) activity in a cell in said subject.

4. The method of claim 2, whereby the composition comprises between about 0.5 and 20 mg/kg/day caffeine.

5. The method of claim 1, whereby the step of administering is via intraperitoneal, parenteral, subcutaneous, intravenous injection.

6. A method of increasing the survival of a subject afflicted with sepsis associated myocardial dysfunction, comprising the step administering to said subject a composition comprising a therapeutically effective amount of a methylxanthine compound.

7. The method of claim 6, whereby said methylxanthine compound is caffeine.

8. The method of claim 6, whereby said methylxanthine compound increases cytochrome oxidase (CcOX) activity in a cell in said subject.

9. The method of claim 7, whereby the composition comprises between about 0.5 and 10 mg/kg/day caffeine.

10. A method of inhibiting or suppressing sepsis associated myocardial dysfunction in a subject in need thereof, comprising the step administering to said subject a composition comprising a therapeutically effective amount of a methylxanthine compound.

11. The method of claim 10, whereby said methylxanthine compound is caffeine.

12. The method of claim 10, whereby said methylxanthine compound increases cytochrome oxidase (CcOX) activity in a cell in said subject.

13. The method of claim 11, whereby 0.5-20 mg/kg/day caffeine is administered to said subject.

14. A method of reducing the symptoms associated with sepsis associated myocardial dysfunction in a subject in need thereof, comprising the step administering to said subject a composition comprising a therapeutically effective amount of a methylxanthine compound.

15. The method of claim 14, whereby said methylxanthine compound is caffeine.

16. The method of claim 14, whereby said methylxanthine compound increases cytochrome oxidase (CcOX) activity in a cell in said subject.

17. The method of claim 15, whereby the composition comprises between about 0.5 and 20 mg/kg/day caffeine.

18. The method of claim 1, wherein the methylxanthine compound is theobromine or theophylline.

19. The method of claim 6, wherein the methylxanthine compound is theobromine or theophylline.

20. The method of claim 10, wherein the methylxanthine compound is theobromine or theophylline.

21. The method of claim 14, wherein the methylxanthine compound is theobromine or theophylline.

* * * * *